(12) United States Patent
Vince et al.

(10) Patent No.: US 7,542,873 B2
(45) Date of Patent: Jun. 2, 2009

(54) METHOD AND APPARATUS FOR DETERMINING PARTICLE PARAMETER AND PROCESSOR PERFORMANCE IN A COAL AND MINERAL PROCESSING SYSTEM

(75) Inventors: Andrew Vince, Mackay (AU); Bruce Andrew Firth, Bellbowrie (AU); Shenggen Hu, West Lake (AU)

(73) Assignee: BM Alliance Coal Operations Pty Ltd (AU)

( * ) Notice: Subject to any disclaimer, the term of this patent is extended or adjusted under 35 U.S.C. 154(b) by 121 days.

(21) Appl. No.: 10/558,126

(22) PCT Filed: May 20, 2004

(86) PCT No.: PCT/AU2004/000674

§ 371 (c)(1),
(2), (4) Date: Nov. 7, 2006

(87) PCT Pub. No.: WO2004/106897

PCT Pub. Date: Dec. 9, 2004

(65) Prior Publication Data

US 2007/0095168 A1    May 3, 2007

(30) Foreign Application Priority Data

May 28, 2003  (AU) .............................. 2003902667
Jul. 17, 2003  (AU) .............................. 2003903724

(51) Int. Cl.
*G06F 11/30* (2006.01)
*G21C 17/00* (2006.01)

(52) U.S. Cl. ...................................... 702/182
(58) Field of Classification Search .................. 702/23, 702/26, 137, 170, 172, 182
See application file for complete search history.

(56) References Cited

U.S. PATENT DOCUMENTS 4,226,714 A  *  10/1980  Furness et al. .............. 210/723

(Continued)

FOREIGN PATENT DOCUMENTS

DE    19751591    *    9/1999

(Continued)

OTHER PUBLICATIONS

Derwent Abstract, DE 19751591, Sep. 1999.*

*Primary Examiner*—Michael P Nghiem
(74) *Attorney, Agent, or Firm*—Brinks Hofer Gilson & Lione; G. Peter Nichols (57) ABSTRACT

An image (100) of particulate material, such as an X-ray image of coal, is captured and processed to determine a parameter of the material, such as particle density or particle size distribution. The performance or efficiency of a processing system, such as a dense medium separator, can be evaluated by determining parameters of the material before entry to and after exit from the processing system. The parameter is determined by comparing image characteristics (relating to statistical features), to a predetermined set of image characteristics. If the image (100) is obtained by transmission of radiation through the material, accuracy can be improved by measuring the thickness of the material.

41 Claims, 7 Drawing Sheets

U.S. PATENT DOCUMENTS

| | | | |
|---|---|---|---|
| 4,470,901 A * | 9/1984 | Burgess | 209/1 |
| 4,731,176 A * | 3/1988 | Macdonald | 209/166 |
| 5,519,793 A | 5/1996 | Grannes | |
| 6,212,943 B1 * | 4/2001 | Maltby et al. | 73/61.49 |
| 6,513,124 B1 * | 1/2003 | Furuichi et al. | 713/322 |
| 2004/0066890 A1 * | 4/2004 | Dalmijn et al. | 378/57 |
| 2006/0196814 A1 * | 9/2006 | Vince | 210/85 |

FOREIGN PATENT DOCUMENTS

| | | |
|---|---|---|
| EP | 0 226 430 | 9/1986 |
| GB | 2075867 * | 11/1981 |
| GB | 2188752 * | 10/1987 |
| JP | 05-230463 | 9/1993 |
| JP | 09-264851 | 10/1997 |
| JP | 2000-329683 | 11/2000 |
| RU | 2149379 | 5/2000 |
| WO | WO 97/14950 | 4/1997 |
| WO | WO 02/50521 | 6/2002 |
| WO | WO 2004/062809 | 7/2004 |

* cited by examiner

METHOD AND APPARATUS FOR DETERMINING PARTICLE PARAMETER AND PROCESSOR PERFORMANCE IN A COAL AND MINERAL PROCESSING SYSTEM

This application claims priority to PCT Application Serial No. PCT/AU 2004/000674 filed May 20, 2004 published in English on Dec. 9, 2004 as PCT WO 2004/106897; to Australian Patent Application No. 2003902667 filed May 28, 2003; and to Australian Patent Application No. 2003903724 filed Jul. 17, 2003, the entire contents of all three of which are incorporated herein by reference.

FIELD OF THE INVENTION

This invention relates to a method and apparatus for determining a parameter of a particle, and method and apparatus for determining processor performance.

The invention has application to a particulate material processing system and, in particular, a system which processes minerals and carbonaceous solids such as coal, iron ore, manganese, diamonds, and other materials. The invention has particular application to the processing of coal, and will be further described in relation to the processing of coal. However, it should be understood that the invention is applicable to processing other materials including, but not restricted to, those mentioned above.

The invention also concerns the determination of a parameter of a particle. The determination of the parameter may be used in relation to the determination of processor performance, or may be used in environments other than that environment simply for determining the parameter of a particle for other reasons.

BACKGROUND OF THE INVENTION

Raw coal is mined from the ground and is processed to provide a desirable commercial product. Raw coal includes a certain amount of gangue mineral content which, following combustion under standard condition, leaves a solid ash residue. Saleable coal most preferably has a fixed ash specification limit which is normally specified in contractual agreements between the producer and the purchaser. A typical example of an ash specification for high quality coking coal is 10%. If the ash level of produced coal increases above this level, the product may still be saleable but its price is deleteriously affected and/or some penalties for the producer may be incurred.

Raw coal after mining may be separated into a particular particle size by a screen mesh type or other classification-type device to separate the raw coal into predetermined particle sizes defined by, for example, the screen aperture size of the screen separator.

The separated coal of the desired size is then supplied to a processor, in this example a dense medium separator. There are a number of different dense medium separators currently in use depending on the size of particles being treated. For example, large lumps may be processed in heavy medium drums, heavy medium baths, heavy medium vessels, larcodems etc, and smaller but still coarse particles may be processed in heavy medium cyclones, heavy medium cycloids etc. Note that the words "heavy" and "dense" can be used interchangeably in this context. These types of heavy medium devices use a benign or inert finely ground powder of medium solids (such as magnetite or ferro-silicon) slurried in water to form a dense medium whose density can be controlled by the proportion of solids in the slurry. Mixing the raw coal with the dense medium enables separation on the basis of its density relative to the density of the dense medium. For example, coal with an ash level of 10% may be separable from higher ash components of the raw coal by adding the raw coal to a dense medium with a density of, for example, 1400 kg/m$^3$. In this example, the 10% ash product coal might float clear of the higher ash material which might tend to sink in the dense medium. The material that floats would report to the overflow outlet of a separator and that which sinks would report to the underflow outlet.

For the specific case of a dense medium cyclone, it is separating efficiency of the coal particles that is often critical to maximising recovery and grade. The accepted industry standard for measuring efficiency is the partition coefficient curve with its characteristic $D_{50}$ and Ep parameters. The $D_{50}$ is the separating density of the particles and the Ep is a measure of the sharpness of the separation (a higher value of Ep indicates more misplacement of particles and hence a lower efficiency). Whilst the $D_{50}$ of a separation is strongly related to the medium density, there are machine effects that lead to, almost invariably, the $D_{50}$ being a little higher than the medium density. The extent to which it is greater is dependent on a number of parameters, including, but not limited to, medium density, medium stability, dense medium cyclone pressure, raw coal feed rate, degree of cyclone wave, and variations therein. The overall sharpness of separation is a strong function of variations in each of these parameters.

Currently partition curves for dense medium cyclones (DMCs), and hence DMC circuit efficiency, are obtained from laboratory washability analysis or tracer testwork at the plant. The data obtained has a degree of accuracy on which the industry has based decisions about the performance level of the DMC and whether corrective actions are necessary. Unfortunately, these tests are characterised by their relatively high cost and long time frame before information becomes available. Infrequent checks find sub-optimal performance resulting in significant coal loss.

Thus, if a particular parameter of a particle can be determined more quickly, it therefore provides the ability for determining processor performance and, if necessary, more quickly taking remedial action to ensure that the processor is operating satisfactorily. The determination of a parameter of a particle is also useful information in environments totally unrelated to processor performance, such as sizing of material produced by crushes, degree of calcination of material, and the like.

SUMMARY OF THE INVENTION

The object of a first invention is to provide a method and apparatus for determining processor performance.

The first invention may therefore be said to reside in a method of determining the performance of a processing apparatus for processing particulate material, the method comprising:

capturing an image of radiation after the radiation has passed through a sample of particulate material to be fed to the processing apparatus, and which radiation has been altered by the particulate material;

capturing an image of radiation after the radiation has passed through a sample of particulate material which has exited from the processing apparatus, and which radiation has been altered by the particulate material;

determining from the captured images a parameter of the particulate material in both the sample of material to be fed to the apparatus, and the sample which exits the apparatus; and determining a performance index of the apparatus by considering the parameter of the material which has exited the apparatus with respect to an expected parameter of the material which has exited the apparatus, having regard to the parameter of the particulate material fed to the apparatus.

The first invention may also be said to reside in a device for determining the performance of a processing apparatus for processing particulate material, the apparatus comprising:

a sensor for capturing an image of radiation after the radiation has passed through a sample of particulate material to be fed to the processing apparatus, and which radiation has been altered by the particulate material, and for capturing an image of radiation after the radiation has passed through a sample of particulate material which has exited from the processing apparatus, and which radiation has been altered by the particulate material; and processing means for determining from the captured images a parameter of the particulate material in both the sample of material to be fed to the apparatus, and the sample which has exited the apparatus, and for determining a performance index of the apparatus by a consideration of the parameter of the material which has exited the apparatus with respect to an expected parameter of the material which has exited the apparatus having regard to the parameter of the particulate material fed to the apparatus.

Thus, if the expected performance index of the processing apparatus is not in accordance with that which is determined according to the method and apparatus, an indication can therefore be made that the processing apparatus is not performing satisfactorily and remedial action can be taken to correct the processing apparatus. In one specific example, in which the material is coal, and the processing apparatus is a dense medium separator, and the parameter is the density of the particulate material, if the density of the material to be fed to the separator is determined, the density of material which reports to an overflow outlet, and/or the density of material which reports to an underflow outlet, can be estimated. Thus, the partition number (i.e. the amount of material which should be reporting to overflow, compared to that which reports to underflow) can be determined. If it is found that the partition number is not in accordance with that which is expected, this is an indication that the separator is not performing satisfactorily and appropriate correction can be made.

In one embodiment the processing apparatus is a separator and the sample of the material which exits the apparatus is a first sample of material which reports to overflow, and which is to comprise product, and a second sample of material which reports to underflow and which is refuse, and wherein the method is further comprised of capturing an image of radiation which is emitted from the first sample of particulate material, and capturing an image of radiation which is emitted from the second sample of particulate material, and wherein, based on the determined parameters of the particulate material in both the sample of material to be fed to the apparatus, and the sample which has exited the apparatus, a determination of performance index can be made as to how much material should report to overflow and how much should report to underflow if the separator is performing satisfactorily, and from the determination of the parameter of the first sample and the parameter of the second sample, an indication of the amount of material actually reporting to underflow and overflow can be made, and by comparing those amounts with the expected amounts, a determination of the performance index of the separator can be made.

In this embodiment the separator is preferably a dense medium cyclone.

Preferably in this embodiment the parameter is the density of the particulate material or mineral content, and the amount of material which reports to underflow and the amount of material which reports to overflow is determined by the densities or mineral content of material which reports to underflow and the densities or mineral content of material which report to overflow, so that if particular densities or mineral content are reporting to underflow which should in fact report to overflow, a determination that the separator is not performing satisfactorily can be made.

Preferably the radiation is x-ray radiation.

In another embodiment the apparatus is a crusher for crushing the particulate material to a smaller size, and the parameter is the size or density or mineral content of the particulate material.

In a still further embodiment the apparatus is a calcinating apparatus and the parameter is the amount of calcination of the particulate material.

Preferably the alteration of the radiation is the attenuation of the radiation.

Preferably the radiation is captured by the sensor by radiating the particulate material with a source of radiation so that the radiation passes through the particulate material to the sensor.

However, in other embodiments the particulate material may be inherently self-radiating or made self-radiating by including radiation producing material within the particulate material.

Thus, in the preferred embodiment of the device, the device also includes a source of radiation for producing radiation for irradiating the particulate material, so the radiation can emit from the particulate material.

Preferably the sensor and the source of radiation are provided in a housing and a conveyor is provided for conveying the particulate material passed between the source of radiation and the sensor, so the radiation can pass through the particulate material, and so the respective images can be captured by the sensor. Alternatively the particulate material is placed on a stationary flat plate between the source of radiation and the sensor, so the radiation can pass through the particulate material, and so the respective images can be captured by the sensor.

Preferably the sensor is a X-ray linear array detector based various detecting techniques, such as scintillator and photoconductors, or a CCD X-ray detector having a plurality of pixels for forming an image.

Preferably the captured image is made up of a number of pixels, each of which has an intensity level depending on the degree to which the radiation has been attenuated by the particle through which the radiation passes. Preferably the intensity values include grey level values and RGB colour values.

The determination of the parameter preferably includes the steps of generating local image windows within which only one particle or a group of overlapped particles presents by identifying boundaries of individual particles or groups of overlapped particles, calculating image characteristics of each identified local image window, calculating indicator variables summarising the information contained in the image characteristics by multivariate statistical methods, such as principal component analysis (PCA) and partial least-squares (PLS) and determining from indicator variables at least one parameter of each particle or a group of overlapped particles in the particulate material using a predictive mathematical model.

The image characteristics preferably include but are not restricted to statistical features based on grey-level or RGB colour histogram which is a plot of the frequency of values of an intensity versus intensities of pixels with a local image window, textures features based on grey-level co-occurrence matrix (also called spatial grey-level dependence matrix) (reference see: Haralick R. M., Shanmugam K. and Dinstein I. IEEE Transactions on Systems, Man and Cybernetics, SMC-3, 1973. pp601-621), Gabor features based on Gabor filters and features based wavelet transforms.

The statistical features based on grey-level or RGB colour histogram preferably include but are not restricted to total number of pixels, mean, median, standard deviation, kurtosis and skew. The textures features based on grey-level co-occurrence matrix preferably include but are not restricted to entropy, contrast, correlation, energy, local homogeneity, maximum probability, sum entropy and difference entropy.

In one embodiment of the invention, the method includes obtaining a measure of the thickness of the material to provide a thickness value and providing the thickness value as a further characteristic feature to determine the parameter.

In one embodiment, the thickness measure is obtained by light sources to illuminate the material and cameras for detecting the illuminated material so that a three-dimensional image of the material is obtained from which a thickness value at each point of a particulate material can be determined. However, the thickness value could be obtained by other techniques.

The predictive mathematical model for the determination of the parameter preferably include but are not restricted to artificial neural networks and multivariate regression models.

It is preferred that the method includes the step of training and validating an artificial neural network model with a number of calibration samples with captured X-ray images and known parameters of the particulate material.

The method further includes calculating parameters in a predictive mathematical model using a number of image characteristics or indicator variables with known parameters of the particulate material.

A second invention is concerned with determining the parameter of a particle. This invention has application in the determination of a parameter for use in the previous invention, but also has applicability to determining a parameter of a particle for reasons unrelated to the first invention. Thus, this invention may be used in any environment where it is desirable to determine a particular parameter of particulate material.

The second invention may be said to reside in a method of determining a parameter of particulate material, comprising:

capturing an image of radiation after the radiation has passed through a sample of the particulate material, and which radiation has been altered by the particulate material;

generating local image windows within which only one particle or a group of overlapped particles presents by identifying boundaries of individual particles or groups of overlapped particles;

determining a set of image characteristics relating to statistical features, textures features, Gabor features and features based wavelet transforms;

comparing the set of image characteristics with a predetermined set of image characteristics relating to the particulate material; and determining the parameter from the comparison.

This invention may also be said to reside in an apparatus for determining the parameter of a particle, comprising:

a sensor for capturing an image of radiation after the radiation has passed through a sample of the particulate material, and which radiation has been altered by the particulate material; and a data processor for generating local image windows within which only one particle or a group of overlapped particles presents by identifying boundaries of individual particles or groups of overlapped particles, and determining a set of image characteristics relating to statistical features, textures features, Gabor features and features based wavelet transforms, comparing the set of image characteristics with a predetermined set of image characteristics relating to the particulate material, and determining the parameter from the comparison.

Thus, according to this aspect of the invention, the parameter of the particle can be quickly determined by capturing images of samples of the particulate material, and processing the image to determine the parameter based on a comparison of determined characteristics with a predetermined set of characteristics relating to that type of particle.

Preferably the parameter is the density of the particulate material.

Preferably the radiation is x-ray radiation.

Preferably the alteration of the radiation is the attenuation of the radiation.

Preferably the radiation is captured by the sensor by illuminating the particulate material with a source of radiation so that the radiation passes through the particulate material to the sensor.

However, in other embodiments the particulate material may be inherently self-radiating or made self-radiating by including radiation producing material within the particulate material.

Thus, in the preferred embodiment of the device, the device also includes a source of radiation for producing radiation for irradiating the particulate material, so the radiation can pass through the particulate material.

Preferably the sensor and the source of radiation are provided in a housing and a conveyor is provided for conveying the particulate material passed between the source of radiation and the sensor, so the radiation can pass through the particulate material, and so the respective images can be captured by the particulate material.

Alternatively the particulate material is placed on a stationary flat plate between the source of radiation and the sensor, so the radiation can pass through the particulate material, and so the respective images can be captured by the sensor.

Preferably the sensor is a X-ray linear array detector based various detecting techniques, such as scintillator and photoconductors, or a CCD X-ray detector having a plurality of pixels for creating the images.

Preferably the captured image is made up of a number of pixels, each of which has an intensity level depending on the degree to which the radiation has been attenuated by the particle through which the radiation passes.

Preferably the intensity values include grey level values and RGB colour values.

Preferably the parameter is determined by generating local image windows within which only one particle or a group of overlapped particles presents by identifying boundaries of individual particles or groups of overlapped particles, determining a set of image characteristics relating to statistical features, textures features, Gabor features and features based wavelet transforms, comparing the set of image characteristics with a predetermined set of image characteristics relating to the particulate type, and determining the parameter from the comparison of the set of image characteristics with the predetermined set of image characteristics.

Preferably the set of characteristics is selected from a plurality of characteristics including total number of pixels, mean, median, standard deviation, kurtosis, skew, entropy, contrast, correlation, energy, local homogeneity, maximum probability, sum entropy, difference entropy and features based on Gabor filters and wavelet transforms.

Preferably the determination of a parameter is performed by intelligent data analysis of image characteristics extracted from the captured image.

Preferably the apparatus includes a material thickness measuring device for providing a measure of the thickness of the material so that the thickness measure may be used as one of the characteristics to enable the parameter to be determined.

In one embodiment the device comprises light sources to illuminate the material, and cameras for detecting the illuminated material so that a three-dimensional image of the material is created from which a thickness measurement can be determined.

The intelligent information processing technique may include artificial neural networks, generic algorithms, or multi-variable correlation.

Preferably a X-ray image of calibration sample material is captured in which the parameter is known and determining a set of image characteristics relating to that parameter of the calibration material.

Preferably the image characteristics are selected based on those image characteristics which most accurately relate to the known parameter of the calibration material.

Preferably the number of characteristics in the set of image characteristics is as low as possible to provide the required degree of accuracy and level of confidence in the determined parameter.

BRIEF DESCRIPTION OF THE DRAWINGS

A preferred embodiment of the invention will be described, by way of example, with reference to the accompanying drawings in which.

DETAILED DESCRIPTION OF THE PREFERRED EMBODIMENTS

The following is a specific example of a generic dense medium cyclone circuit. It is given as a means only of explaining how the invention can be applied and does not limit the coverage of the invention to the specific example given.

Figure 1:
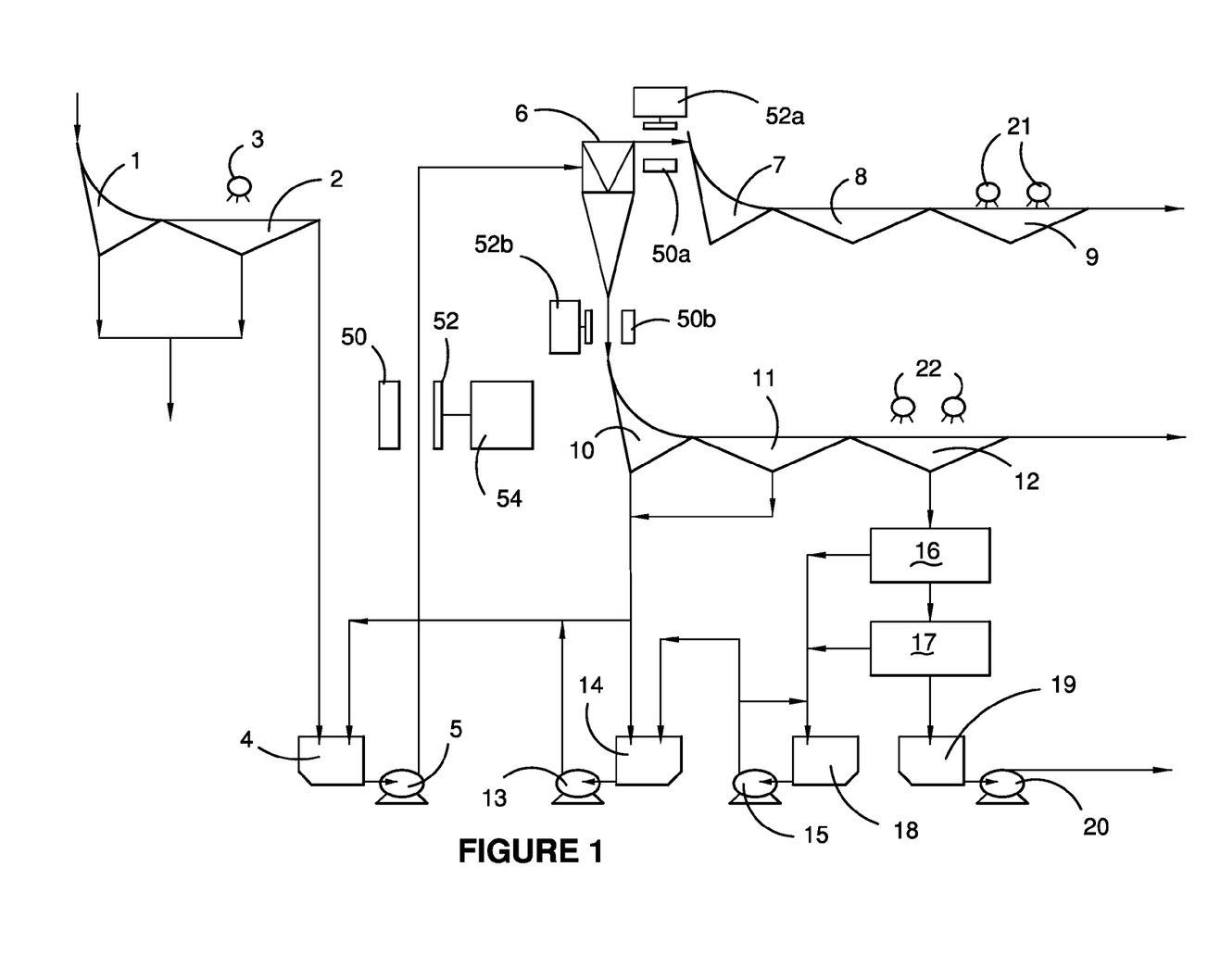
FIG. 1 is an illustrative diagram illustrating apparatus for processing coal with which the preferred embodiment of the invention is used.

Prior to entering the process depicted in FIG. 1, raw coal may be reduced to 50 mm top size. With reference to FIG. 1, raw coal is separated on a sieve bend 1 followed by a vibratory screen 2 with wash water addition 3. This device removes fine particles, typically 2-0.2 mm, from the raw coal and all the undersize is processed in devices not mentioned here. The oversize material gravitates to sump 4 from which it is pumped 5 to the dense medium cyclone 6. It will be noted on FIG. 1 that dense medium is added to the coarse coal particles in the dense medium cyclone feed sump 4. The coarse raw coal is separated in the dense medium cyclone 6 to produce a lower ash product and a higher ash reject. The product is separated from the dense medium on sieve bend 7 and drain 8 and rinse screen 9. The sieve bend and drain screens remove the bulk of the dense medium which can then recycled to the dense medium sump 14. The rinse screen 9 uses water addition 21, 22 (dirty and clarified) to aid the removal of medium adhering to the coal particles. Rinse screen underflow is significantly diluted and must be concentrated such that the water is removed before it can be reused in the operation of the dense medium cyclone. Similar sieve bend 10, drain 11 and rinse 12 screen recovery of dense medium occurs for the dense medium cyclone underflow material.

The diluted dense medium is dewatered with magnetic separators 16 and 17. The recovered dense medium is passed to the over-dense sump 18 from where it is pumped 15 to the dense medium sump 14. The separated water is recycled for use elsewhere in the plant, including water addition to the screening operations described above.

The apparatus embodying the invention is shown in FIG. 1 and comprises an x-ray source 50, a detector 52 such as a CCD array or the like, and a processor 54 connected to the sensor 52, which are provided to capture images of the material to be fed to the cyclone 6. Similarly, an x-ray source 50a and the detector 52a are provided on the overflow line to which product reports and an x-ray source 50b and a detector 52b are provided on the overflow line to which refuse reports. The x-ray sources and sensors 52 are properly shrouded for safety reasons, and the particulate material passes between the x-ray sources 50 and the detectors 52. It should be understood that whilst FIG. 1 shows three sets of x-ray sources and detectors for capturing images of the material fed to the cyclone 6, the material received at the overflow from the cyclone 6 and the material received at the underflow from the cyclone 6, this is merely illustrative and represents a situation which may occur if it is intended to provide permanent on-line monitoring of the cyclone 6. However, the more likely arrangement is that the x-ray source 50 and detector 52 would be provided in its own housing with a conveyor assembly located between the x-ray source 50 and the detector 52 onto which samples of the material to be fed to the cyclone 6 can be located to capture an image, and then sample of material received at the overflow can be located to capture an image, and then sample of material which is received at the underflow can be located to capture an image. Preferably the sample material is simply deposited on a conveyor which runs the sample material passed the x-ray source 50 and the detector 52, with the various samples simply being received from the feed line, overflow and outflow. The sample material is preferably deposited on the conveyor and spread to provide a relatively thin body of sample material through which the x-ray radiation passes from the source 50 to the detector 52.

The sensors 52 are connected to an electronic processor 54 for processing the data captured by the sensors 52. If the system is on-line, then the sensors 50a and 50b are also connected to the processor 54. However, if the system is not on-line and the feed, overflow and underflow samples are simply taken to the device, then obviously only one x-ray source 50, one sensor 52 and one processor 54 is provided. In an alternative arrangement, the processor 54 need not be provided on the device and could be remote from the device with the data captured by the sensor 52 simply being taken to the processor and input into the processor for processing.

Figure 2:
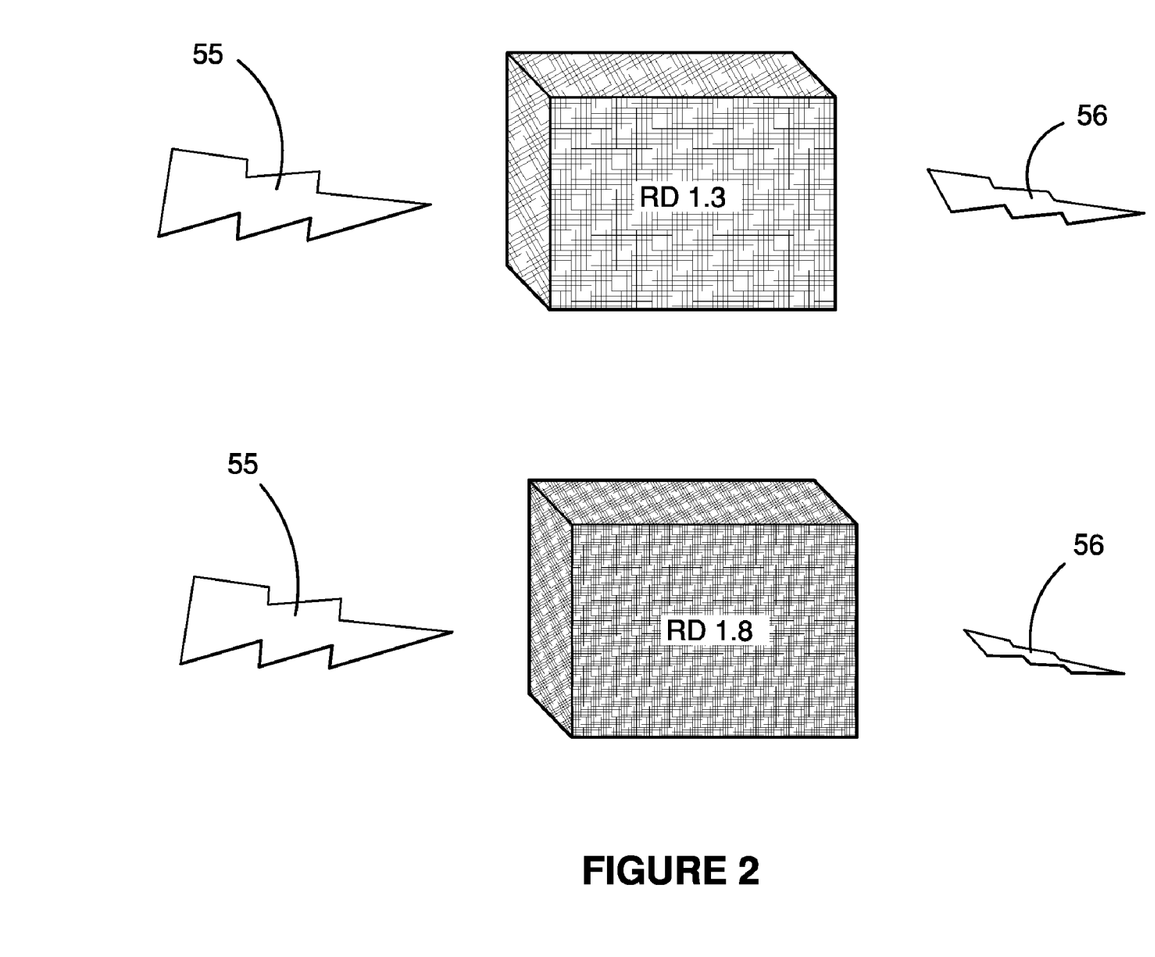
FIG. 2 is a view illustrating the concept of the invention in which different densities attenuate x-ray radiation by different amounts.

FIG. 2 is a diagram which simply illustrates the attention of x-ray radiation 56 produced by the x-ray source 50 by the particulate material having an Rd of 1.3 and an Rd of 1.8 for example. The "bolts" 56 on the right hand side of the drawing simply illustrate the attenuation of the radiation 55.

In order to illustrate the concept of the invention, samples of de-sliming screen overflow from a coal processing plant were obtained and laboratory prepared washability size and density fractions RD (50×16, 16×4, 4×2 and 2×0.5 mm with floats 1.3, 1.35, 1.4, 1.45, 1.5, 1.6 1.7, 1.8, 1.9 and 2.0 relative densities).

Figure 3:
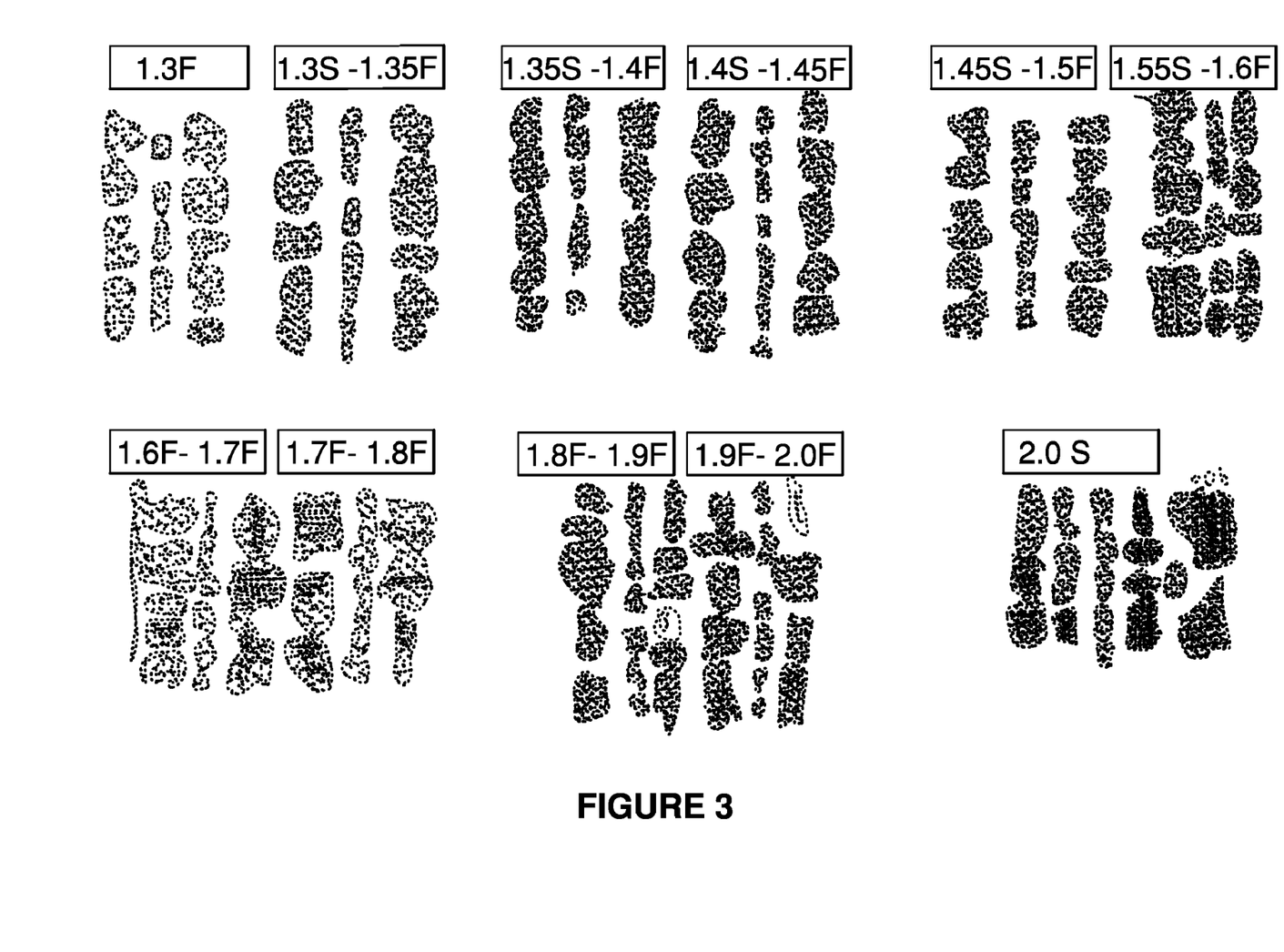
FIG. 3 are sample X-ray images of particulate material with different densities.
Figure 4:
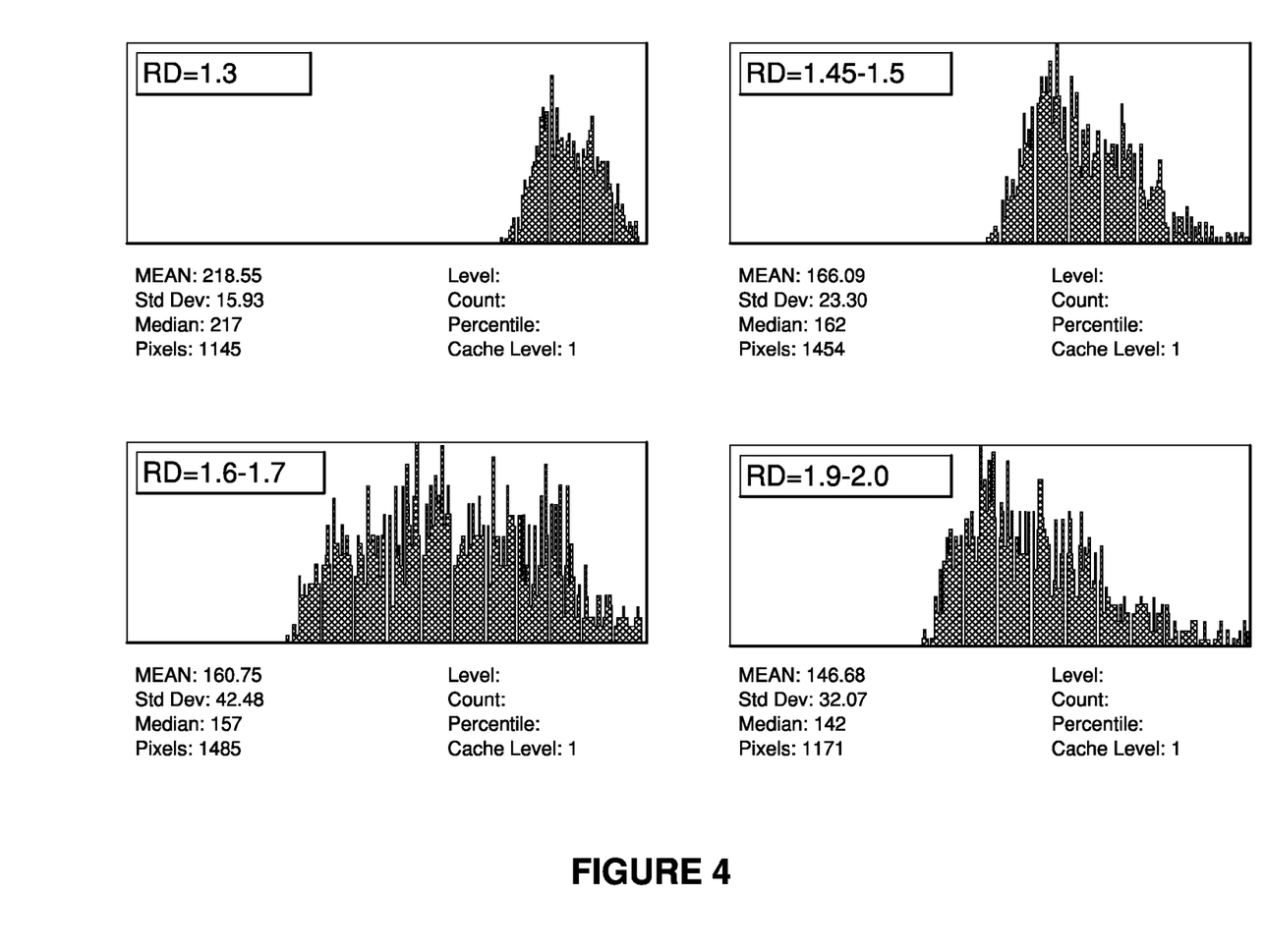
FIG. 4 are histograms of captured x-ray images of coal samples.

An x-ray scanner such as a model PXM scanner was used to provide the source of x-ray radiation 50 and also the sensor 52 and attenuation images for the above-mentioned sample were captured. Examples of the images are shown in FIG. 3. It can be seen that the grey level of particle image decreases with an increase in the coal particle density (i.e. the higher of the particle Rd, the darker the particle image). The captured image was made up of a number of pixels, each of which has a quantitative level of greyness depending on the degree to which the x-ray has been attenuated by the material in the particle through which the radiation passes. For each particle, the number of pixels with a particular grey level can be plotted against the grey level in the form of a histogram. Examples of the histograms of the particle images are shown in FIG. 4. These histograms move towards the left hand side and become broader with the increase of the particles RD. This is a result of the clean coal being replaced with mineral matter and becoming more heterogeneous in nature.

Figure 5:
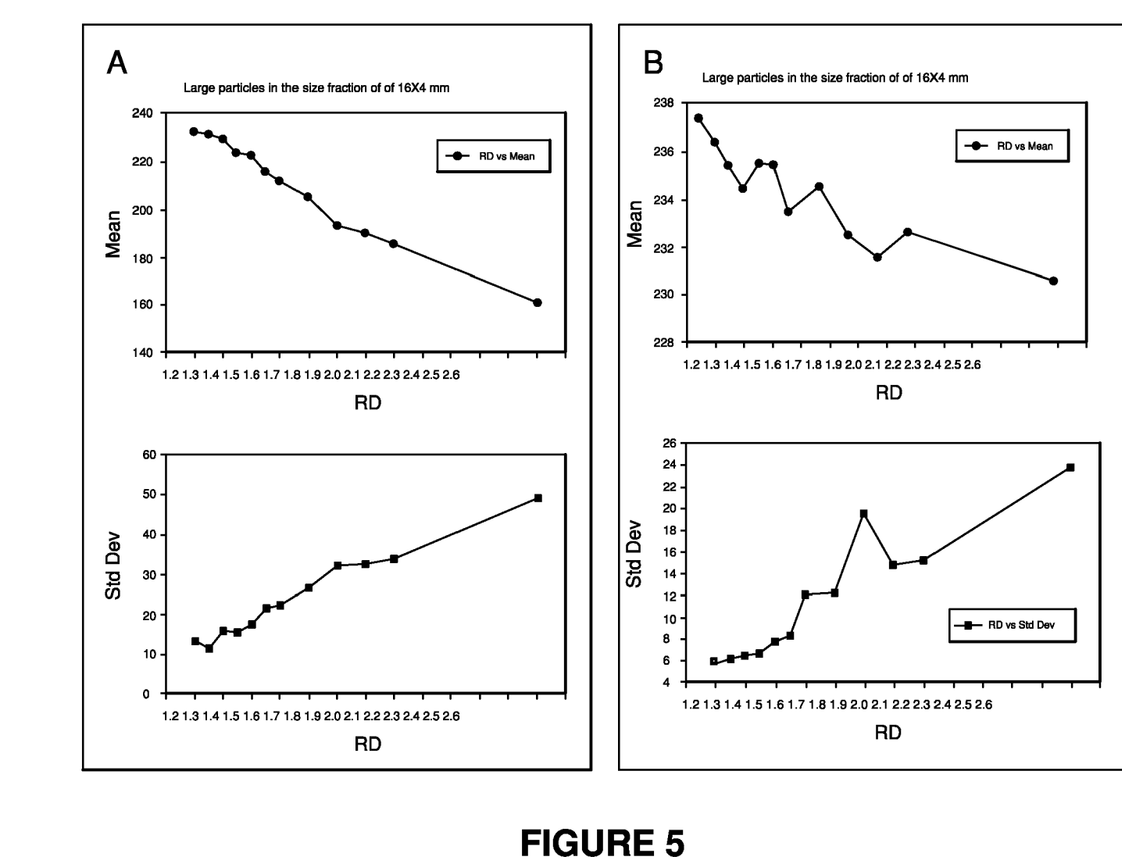
FIG. 5 are plots of relative density (RD) versus mean and standard deviation of histogram for various coal samples.
Figure 6:
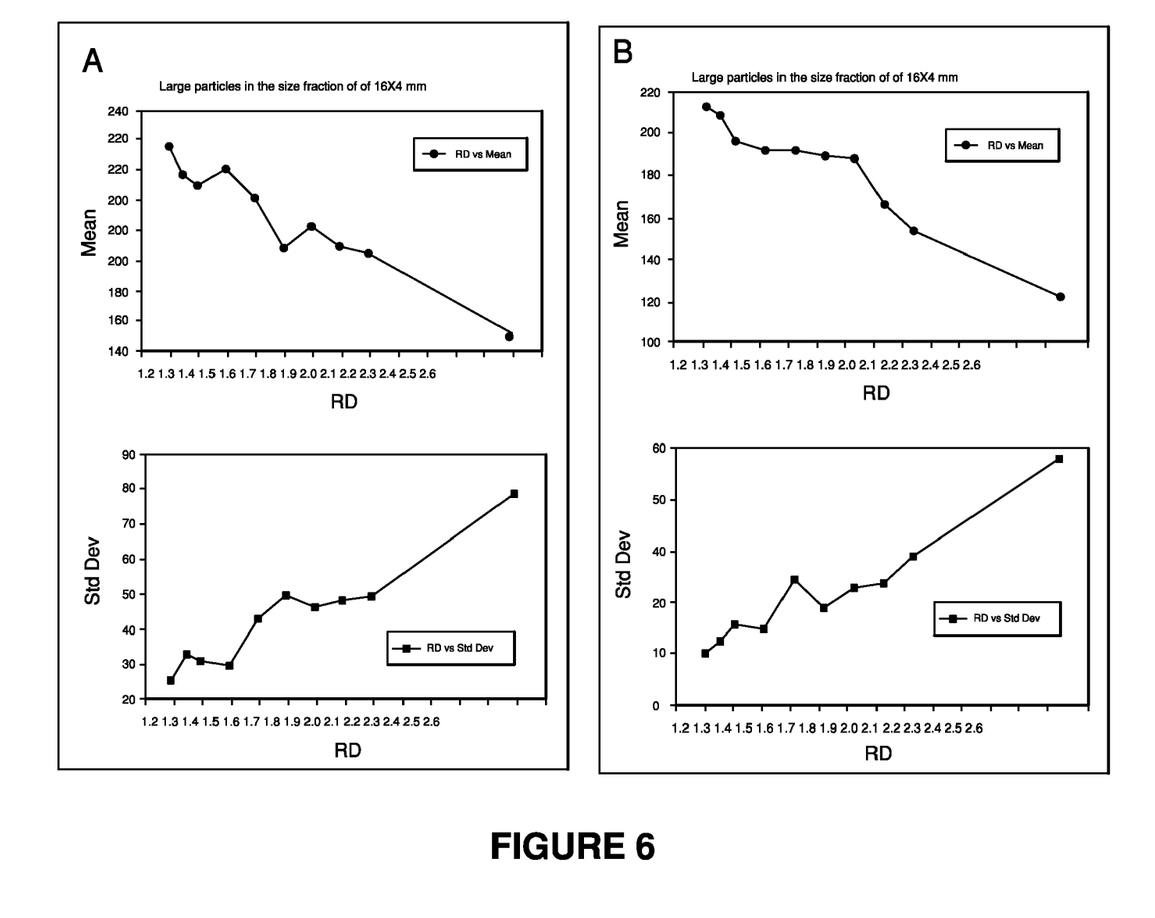
FIG. 6 are plots of relative density (RD) versus mean and standard deviation of histogram for other coal samples.

From the histogram, i.e. the distribution, two parameters, the mean grey level value (GLmean) and the broadness of the distribution as given by the Standard Deviation (GLwidth) distribution can be calculated. These are the two easiest values that can be calculated to describe the distribution, but there are many other factors which can also be employed. Plots of these two parameters versus coal particle relative density (RD) are shown in FIGS. 5 and 6 for particles down to 4 mm in size. It can be seen that the RD is clearly correlated with the GLmean and the GLwidth. The GLmean decreases with an increase in RD and the GLwidth increases with an increase in RD. It is these correlations that provides the basis for the determination of particle density from the X-ray image.

It should be noted that the determination of particle density will not be based solely on the correlation between RD and the two parameters, but based on the intelligent data analysis of all important image characteristics extracted from the particle image. There are a number of image characteristics or parameters extracted from the X-ray image that can be used to increase the accuracy of the density determination. The image characteristics will include not only the GLmean and the GLwidth, but also parameters extracted from particle images, such as median, kurtosis, skew, entropy, contrast, correlation, energy, local homogeneity, maximum probability, sum entropy, difference entropy and features based on Gabor filters and wavelet transforms.

The captured X-ray image of coal particles contains information related to not only the particle density, but also on the particle size, shape and mineral composition and location. Image characteristics extracted from the X-ray image are therefore related to both the coal particle density and other factors.

Thus, by capturing images of a calibration sample such as that described with reference to FIGS. 5 and 6, a set of image characteristics such as mean and standard deviation can be built up for known particle parameter such as known densities and thickness of the calibration sample of particles. This provides a reference for comparison in order to determine the parameter of material from the plan shown in FIG. 1.

In the preferred embodiment of the invention, the images are captured by producing x-ray radiation from an x-ray source and a detector for detecting the attenuated radiation, as has been described above. However, the image could be captured in other ways, such as an RMI image.

Among the various approaches for describing and modelling quantitative relationships that are too complex for analytical methods or empirical rules, artificial intelligence data analysis techniques, particularly the Artificial Neural Network, are preferred for identifying or mapping complex non-linear relations without requiring specific knowledge of the model structure. Artificial Neural Network (ANN) techniques are very efficient and reliable in computation due to the feedforward nature and also have higher tolerance to errors in the input data set than other parameter estimation approaches. A Back-Propagation Artificial Neural Network (BPANN) is used to estimate the coal particle density distribution from the measured X-ray images of coal particles.

Figure 7:
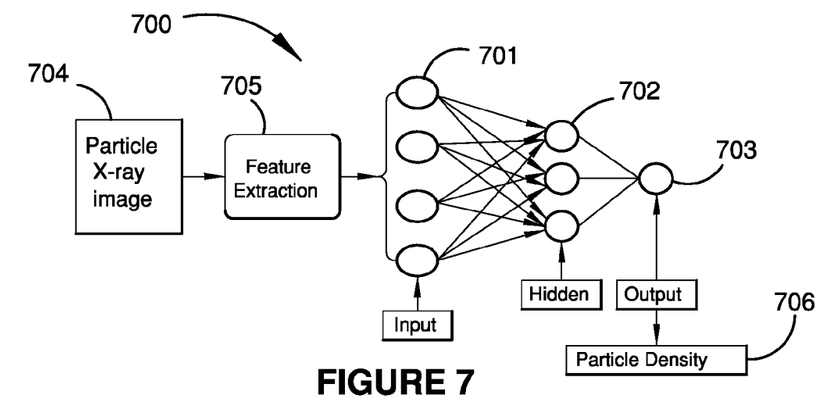
FIG. 7 is a view of the processing according to one embodiment of the invention.

As shown in FIG. 7, the three layered Back-Propagation Artificial Neural Network 700 (BPANN) contains an input layer 701, a hidden layer 702, and an output layer 703. Image data 704 of each particle to the network will be pre-processed 705 to calculate image characteristics, such as mean, standard deviation, median, kurtosis, skew, entropy, contrast, correlation, energy, local homogeneity, maximum probability, sum entropy, difference entropy and features based on Gabor filters and wavelet transforms. These parameters are then directly fed into the neural network to calculate the coal particle density or pre-processed to reduce the number of variables using feature extraction methods, such as principal component analysis (PCA) and partial least-squares (PLS) before fed into the neural network 700 to calculate the coal particle density 706.

Figure 8:
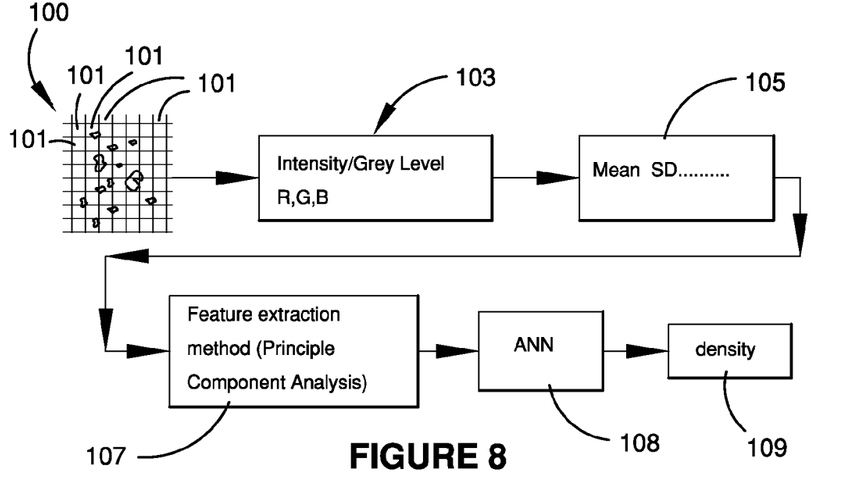
FIG. 8 is a schematic diagram relating to the preferred embodiment of the invention.

FIG. 8 shows the preferred embodiment of the invention in which the image captured by the sensor 50 is processed in order to determine the density of the particulate material. Obviously the same procedure is performed for the sample material to be fed to the cyclone 6, the overflow material from the cyclone 6, and the underflow material from the cyclone 6. Similarly, particulate material from any other environment can also be used to provide the image which is then processed to determine the density of that material.

As is shown in FIG. 8, the image 100 captured by the X-ray sensor 52 is in the form of an array of pixels 101, all of which have an intensity value having regard to the amount of radiation which impinges on the pixel when the image is captured. The radiation which is provided from the source 50 is altered by passage through the particulate material and, in particular, is attenuated by that material, depending on the particular characteristics such as the density of the material.

Thus, the intensity of each of the pixels 101 in grey scale or RGB colour values all differ depending on the intensity of the radiation which impinges on those pixels, which in turn depends on the density of the material through which the radiation passes.

Thus, the X-ray sensor 52 is able to produce an X-ray image from which certain image characteristics can then be determined, such as mean, standard deviation, together with the other characteristics which have been previously mentioned. These image characteristics are determined and are illustrated at 105 in FIG. 8.

These image characteristics therefore provide raw data which is pre-processed at step 107 by way of principle component analysis (PCA) in order to extract features to provide to artificial neural network illustrated at step 108 in FIG. 8. The feature extraction method is intended to extract a less number of features which can summarise the set of image characteristics. Most preferably, as few characteristics as is possible are selected to provide the degree of accuracy and confidence in the end density measurement which is to be made.

The pre-processing to extract the features of step 107 therefore provides an input to the network at step 108. The artificial neural network at step 108 then processes the input data to determine the particle density using the network weight coefficient matrix predetermined in the training stage.

Figure 9:
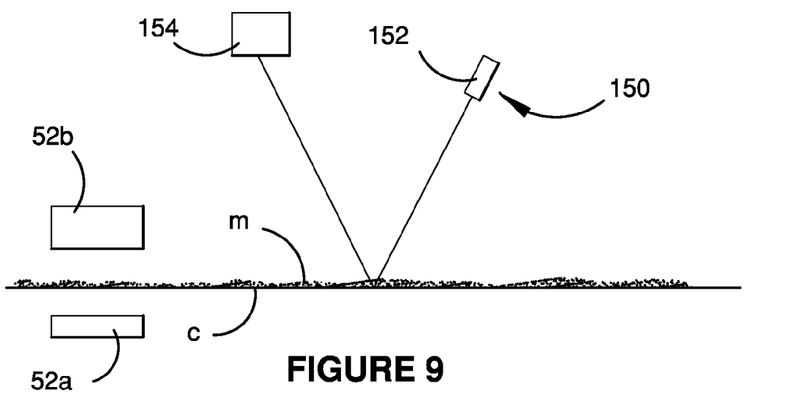
FIG. 9 is a schematic view of a device for obtaining a thickness measure used in the preferred embodiment of the invention.

With reference to FIG. 9, because the determination of the parameter such as density in the preferred embodiment is made by measuring x-ray radiation which is passed through the material, the measurements are based on the attenuation of the x-ray radiation. Because the sample material may have different sizes and generally take different shapes, even if laid out as an extremely thin layer, the attenuation will depend on the actual thickness of the material through which the x-ray radiation passes. For example, if the material has a slab like shape which is relatively thin, a certain amount of attenuation will occur. If the material has exactly the same density, but is of a block-type shape or more irregular shape, more attenuation may be expected because x-ray radiation is passing through a greater thickness of the same material. Thus, the measurement of the actual parameter which is used to determine the performance of the apparatus, or simply to obtain a measure of the parameter per se can be greatly improved if a thickness measure for the material is provided together with the above-mentioned features to the neural network for processing to determine the parameter.

Thus, in the embodiment of FIG. 9, the x-ray source 52b and detector 52a (for example) are shown schematically for providing the previously mentioned image of the material M which may be provided on a conveyor belt C. Similar thickness measurements can also be made in association with the other sensor and detector pairs 50a, 52a and 50b, 52b described with reference to FIG. 1.

Preferably the device 150 for determining the thickness measure comprises a IVP ranger M50 device. This device includes a laser light source 152 and a camera 154. The device 150 also comes with its own software for creating an image value from the image captured by the camera 154. The laser 152 provides a thin spread out fan-like shape of light which extends across the material M and a three-dimensional image of the illuminated material M is captured by the camera 154. By processing within the device of the three-dimensional image, a thickness measure of the material M can be obtained which can be related back to the measurements which are being obtained by the detector 52a.

Thus, the features which are provided to the neural network at step 108 in FIG. 8 can include the thickness measure which will greatly improve results because a further characteristic feature indicative of actual thickness of the material is provided which can be related to attenuation values and other characteristic features to thereby improve the accuracy of the density measurements which are obtained.

In one embodiment of the invention, the type of x-ray source and detector is in the form of a conventional x-raying machine which has a generally L-shaped detector. Material passes the x-ray source and detector as a relatively thin layer on a belt. This results in a generally fan-shaped x-ray beam and a particular spatial distribution of the camera or detector elements. Due to this, the x-ray image for the same particle may change with its location in the longitudinal direction of the belt upon which the particles are conveyed. Therefore, image characteristics for the same particles depend not only on the density and thickness of the particle, but also the location of the particle on the belt. To take this effect into account, the centre location of each identified particle in the image frame may also be used as an input for the mathematical modelling described with reference to FIGS. 7 and 8. If different forms of detectors with suitable resolution are utilised, this is not necessary.

In the claims which follow and in the preceding description of the invention, except where the context requires otherwise due to express language or necessary implication, the word "comprise", or variations such as "comprises" or "comprising", is used in an inclusive sense, i.e. to specify the presence of the stated features but not to preclude the presence or addition of further features in various embodiments of the invention.

The invention claimed is:

1. A method of determining the performance of a processing apparatus for processing particulate material, the method comprising:

capturing with a first sensor an image of radiation after the radiation has passed through a sample of particulate material to be fed to the processing apparatus, and which radiation has been altered by the particulate material;

capturing with a second sensor an image of radiation after the radiation has passed through a sample of particulate material which has exited from the processing apparatus, and which radiation has been altered by the particulate material;

determining from the captured images a parameter of the particulate material in each of the sample of material to be fed to the apparatus, and the sample which exits the apparatus; and determining a performance index of the apparatus by comparing the parameter of the material which has exited the apparatus with respect to an expected parameter of the material which has exited the apparatus, and having regard to the parameter of the particulate material fed to the apparatus.

2. The method of claim 1 wherein the processing apparatus is a separator and the sample of the material exiting the apparatus is a first sample of material directed to overflow comprising product, and a second sample of material directed to underflow and comprising refuse, and wherein the method is further comprised of capturing an image of radiation which is emitted from the first sample of particulate material, and capturing an image of radiation which is emitted from the second sample of particulate material, and determining a parameter of the particulate material of both the sample of material to be fed to the apparatus, and the sample which has exited the apparatus, such that a determination of performance index can be made as to how much material should be expected to be directed to overflow and how much should be expected to be directed to underflow if the separator is performing satisfactorily, and from the determination of the parameter of the first sample and the parameter of the second sample, an indication of amounts of material actually directed to underflow and overflow can be made, and by comparing amounts actually directed to underflow and overflow with the expected amounts to be directed to underflow and overflow, a determination of the performance index of the separator can be made.

3. The method of claim 2 wherein the separator is a dense medium cyclone.

4. The method of claim 3 wherein the parameter is the density of the particulate material or mineral content, and the amount of material which is directed to underflow and the amount of material which is directed to overflow is determined by the densities or mineral content of material which is directed to underflow and the densities or mineral content of material which is directed to overflow, so that if particular densities or mineral content are directed to underflow which should in fact be directed to overflow, a determination that the separator is not performing satisfactorily can be made.

5. The method of claim 2 wherein the determined parameter is the density of the particulate material or mineral content, and the amount of material directed to underflow and the amount of material directed to overflow is determined by the densities or mineral content of material directed to underflow and the densities or mineral content of material directed to overflow, so that if particular densities or mineral content are directed to underflow which should in fact be directed to overflow, a determination that the separator is not performing satisfactorily can be made.

6. The method of claim 1 wherein the radiation is x-ray radiation.

7. The method of claim 1 wherein the apparatus is a crusher for crushing the particulate material to a smaller size, and the parameter is the size or density or mineral content of the particulate material.

8. The method of claim 1 wherein the apparatus is a calcinating apparatus and the parameter is the amount of calcination of the particulate material.

9. The method of claim 1 wherein the alteration of the radiation is the attenuation of the radiation.

10. The method of claim 1 wherein the radiation is captured by the first or second sensor by radiating the particulate material with a source of radiation so that the radiation passes through the particulate material to the sensor.

11. The method of claim 1 wherein the particulate material is inherently self-radiating or made self-radiating by including radiation producing material within the particulate material.

12. The method of claim 1 wherein the captured image is made up of a number of pixels, each of which has an intensity level depending on the degree to which the radiation has been attenuated by the particle through which the radiation passes.

13. The method of claim 12 wherein the intensity level is at least one of a gray scale and an RGB colour.

14. The method of claim 1 wherein the determination of the parameter includes the steps of generating local image windows within which only one particle or a group of overlapped particles presents by identifying boundaries of individual particles or groups of overlapped particles, calculating image characteristics of each identified local image window, calculating indicator variables summarising the information contained in the image characteristics by multivariate statistical methods, and determining from indicator variables at least one parameter of each particle or a group of overlapped particles in the particulate material using a predictive mathematical model.

15. The method of claim 14 wherein the image characteristics are selected from the group consisting of one or more of statistical features based on grey-level or RGB colour histogram which is a plot of the frequency of values of an intensity versus intensities of pixels with a local image window, textures features based on grey-level co-occurrence matrix, Gabor features based on Gabor filters, and features based on wavelet transforms.

16. The method of claim 15 wherein statistical features based on grey-level or RGB colour histogram are selected from the group consisting of one or more of total number of pixels, mean, median, standard deviation, kurtosis and skew, and the textures features based on grey-level co-occurrence are selected from the group consisting of one or more of entropy, contrast, correlation, energy, local homogeneity, maximum probability, sum entropy and difference entropy.

17. The method of claim 15 wherein the method includes obtaining a measure of the thickness of the material to provide a thickness measure and providing the thickness measure as a further characteristic feature to determine the parameter.

18. The method of claim 17 wherein the thickness measure is obtained by light sources to illuminate the material and cameras for detecting the illuminated material so that a three-dimensional image of the material is obtained from which the thickness measure is determined.

19. The method of claim 14 wherein the mathematical model for the determination of the parameter comprises artificial neural networks or multivariate regression models.

20. The method of claim 19 further comprising the step of training and validating the artificial neural network model with a number of calibration samples with captured X-ray images and known parameters and thickness of the particulate material.

21. The method of claim 19 further comprising calculating parameters in a predictive mathematical model using a number of image characteristics or indicator variables with known thickness of the particulate material.

22. A device for determining the performance of a processing apparatus for processing particulate material, the device comprising:
a first sensor for capturing an image of radiation after the radiation has passed through a sample of particulate material to be fed to the processing apparatus, and which radiation has been altered by the particulate material, and a second sensor for capturing an image of radiation after the radiation has passed through a sample of particulate material which has exited from the processing apparatus, and which radiation has been altered by the particulate material; and
data processing means for determining from the captured images a parameter of the particulate material in each of the sample of material to be fed to the apparatus, and the sample which has exited the apparatus, and for determining a performance index of the apparatus by comparing the parameter of the particulate material which has exited the apparatus with respect to an expected parameter of the particulate material which has exited the apparatus and having regard to the parameter of the particulate material fed to the apparatus.

23. The device of claim 22 wherein the processing apparatus is a separator and the sample of the material existing the apparatus is a first sample of material directed to overflow comprising product, and a second sample of material directed to underflow comprising refuse, and wherein the method is further comprised of capturing an image of radiation which is emitted from the first sample of particulate material, and capturing an image of radiation which is emitted from the second sample of particulate material, and the data processing means determines parameters of the particulate material of both the sample of material to be fed to the apparatus, and the sample exiting the apparatus, such that a determination of performance index can be made as to how much material should be expected to be directed to overflow and how much should be expected to be directed to underflow if the separator is performing satisfactorily, and from the determination of the parameter of the first sample and the parameter of the second sample, an indication of amounts of material actually directed to underflow and overflow can be made, and by comparing the amounts actually directed to underflow and overflow with the expected amounts to be directed to underflow and overflow, a determination of the performance index of the separator can be made.

24. The device of claim 23 wherein the separator is preferably a dense medium cyclone.

25. The device of claim 24 wherein the parameter is the density of the particulate material or mineral content, and the amount of material which is directed to underflow and the amount of material which is directed to overflow is determined by the densities or mineral content of material which is directed to underflow and the densities or mineral content of material which is directed to overflow, so that if particular densities or mineral content are directed to underflow which should in fact be directed to overflow, a determination that the separator is not performing satisfactorily can be made.

26. The device of claim 23 wherein the determined parameter is the density of the particulate material or mineral content, and the amount of material directed to underflow and the amount of material directed to overflow is determined by the densities or mineral content of material directed to underflow and the densities or mineral content of material directed to overflow, so that if particular densities or mineral content are directed to underflow which should in fact be directed to overflow, a determination that the separator is not performing satisfactorily can be made.

27. The device of claim 22 wherein the apparatus is a crusher for crushing the particulate material to a smaller size, and the parameter is the size or density or mineral content of the particulate material.

28. The device of claim 22 wherein the apparatus is a calcinating apparatus and the parameter is the amount of calcination of the particulate material.

29. The device of claim 22 wherein the device also includes a first and second source of radiation for producing radiation for irradiating the particulate material, so the radiation can emit from the particulate material to be captured by the first and second sensor, respectively.

30. The device of claim 29 wherein each sensor and each source of radiation are provided in a housing and conveyors are provided for conveying the particulate material passed between each source of radiation and each sensor, so the radiation can pass through the particulate material, and so the respective images can be captured by the sensor.

31. The device of claim 30 wherein each sensor is a X-ray linear array detector based various detecting techniques, such as scintillator and photoconductors, or a CCD X-ray detector having a plurality of pixels for forming an image.

32. The device of claim 22 wherein each captured image of radiation is made up of a number of pixels, each of which has an intensity level depending on the degree to which the radiation has been attenuated by the particle through which the radiation passes.

33. The device of claim 32 wherein the intensity level is at least one of a gray scale level and an RGB colour.

34. The device of claim 22 wherein the processing means is for determination of the parameter by generating local image windows within which only one particle or a group of overlapped particles presents by identifying boundaries of individual particles or groups of overlapped particles, calculating image characteristics of each identified local image window, calculating indicator variables summarising the information contained in the image characteristics by multivariate statistical methods, and determining from indicator variables at least one parameter of each particle or a group of overlapped particles in the particulate material using a predictive mathematical model.

35. The device of claim 34 wherein the image characteristics are selected from the group consisting of one or more of statistical features based on grey-level or RGB colour histogram which is a plot of the frequency of values of an intensity versus intensities of pixels with a local image window, textures features based on grey-level co-occurrence matrix, Gabor features based on Gabor filters, and features based on wavelet transforms.

36. The device of claim 35 wherein the statistical features based on grey-level or RGB colour histogram are selected from the group consisting of one or more of total number of pixels, mean, median, standard deviation, kurtosis and skew.

37. The device of claim 35 further comprising a thickness measuring device for providing a thickness measure of the material.

38. The device of claim 37 wherein the thickness measuring device consists of light sources to illuminate the material and cameras for detecting the illuminated material so that a three-dimensional image of the material is obtained from which the thickness measure is determined.

39. The device of claim 37 wherein the processing means further comprises artificial neural networks or multivariate regression models for providing a predictive mathematical model for the determination of the parameter.

40. The device of claim 39 wherein the processing means is also for training and validating the artificial neural network model with a number of calibration samples with captured X-ray images and known parameters and thickness of the particulate material.

41. The device of claim 39 wherein the processing means is also for calculating parameters in the predictive mathematical model using a number of image characteristics or indicator variables with known thickness of the particulate material.

* * * * *

UNITED STATES PATENT AND TRADEMARK OFFICE
CERTIFICATE OF CORRECTION

PATENT NO. : 7,542,873 B2
APPLICATION NO. : 10/558126
DATED : June 2, 2009
INVENTOR(S) : Andrew Vince et al.

Page 1 of 1

It is certified that error appears in the above-identified patent and that said Letters Patent is hereby corrected as shown below:

In the Claims

In column 12, claim 1, line 51, after "the parameter of the" insert --particulate--.

In column 12, claim 1, line 53, before "material which has exited" insert --particulate--.

In column 13, claim 6, line 34, after "radiation is" replace "x-ray" with --X-ray--.

In column 14, claim 23, line 64, after "the material" replace "existing" with --exiting--.

Signed and Sealed this

Twenty-fourth Day of November, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,542,873 B2 | Page 1 of 1 |
| APPLICATION NO. | : 10/558126 | |
| DATED | : June 2, 2009 | |
| INVENTOR(S) | : Andrew Vince et al. | |

It is certified that error appears in the above-identified patent and that said Letters Patent is hereby corrected as shown below:

Title Page, Item (73) In the "Assignee"

On the face page, column 1, reference numeral 73, immediately after "BM Alliance Coal Operations Pty Ltd (AU)", please insert -- and Commonwealth Scientific And Industrial Research Organisation (AU) --

Signed and Sealed this

Twenty-third Day of March, 2010

David J. Kappos
*Director of the United States Patent and Trademark Office*